United States Patent
AlKhiary et al.

(10) Patent No.: US 11,033,357 B1
(45) Date of Patent: Jun. 15, 2021

(54) METHODS FOR TOOTH EXTRACTION USING A THERMOELECTRIC DEVICE

(71) Applicant: King Abdulaziz University, Jeddah (SA)

(72) Inventors: Yasser AlKhiary, Jeddah (SA); Lulwa AlTurki, Jeddah (SA); Nuha AlRayes, Jeddah (SA)

(73) Assignee: King Abdulaziz University, Jeddah (SA)

(*) Notice: Subject to any disclaimer, the term of this patent is extended or adjusted under 35 U.S.C. 154(b) by 0 days.

(21) Appl. No.: 17/095,790

(22) Filed: Nov. 12, 2020

(51) Int. Cl.
| | | |
|---|---|---|
| *A61B 18/04* | (2006.01) | |
| *A61C 3/14* | (2006.01) | |
| *A61B 18/08* | (2006.01) | |
| *A61B 18/00* | (2006.01) | |

(52) U.S. Cl.
CPC ............. *A61C 3/14* (2013.01); *A61B 18/082* (2013.01); *A61B 2018/00041* (2013.01); *A61B 2018/00321* (2013.01); *A61B 2018/00571* (2013.01); *A61B 2018/00714* (2013.01); *A61B 2018/00761* (2013.01)

(58) Field of Classification Search
CPC .................. A61C 3/14; A61B 18/082; A61B 2018/00714; A61B 2018/00321; A61B 2018/00571; A61B 2018/00041; A61B 2018/00761
See application file for complete search history.

(56) References Cited

U.S. PATENT DOCUMENTS

| | | | |
|---|---|---|---|
| 3,274,995 A | 9/1966 | Eidus | |
| 5,019,038 A | 5/1991 | Linden | |
| 5,324,200 A * | 6/1994 | Vassiliadis | A61B 18/20 433/224 |
| 5,782,827 A * | 7/1998 | Gough | A61B 18/18 606/41 |
| 8,215,955 B2 | 7/2012 | Lee | |
| 2010/0124728 A1 | 5/2010 | Walia | |
| 2011/0200960 A1 | 8/2011 | Colby | |
| 2012/0283798 A1 * | 11/2012 | Tominaga | A61B 18/1477 607/51 |
| 2015/0050617 A1 * | 2/2015 | Marynka Kalmani | A61C 19/063 433/172 |
| 2015/0374456 A1 * | 12/2015 | Colby | A61B 18/1477 433/25 |

* cited by examiner

*Primary Examiner* — Daniel W Fowler
(74) *Attorney, Agent, or Firm* — W & C IP

(57) ABSTRACT

Methods for atraumatic tooth extraction are provided. The methods include inserting an instrument into a pulp canal of a tooth, wherein the instrument comprises a body electrically connected to a heat providing source; and a tip arranged at one end of the body configured for insertion into a pulp canal; heating the tip to provide a temperature sufficient to degenerate periodontal ligament; withdrawing the instrument from the pulp canal; and extracting the tooth.

9 Claims, 3 Drawing Sheets

METHODS FOR TOOTH EXTRACTION USING A THERMOELECTRIC DEVICE

FIELD OF THE INVENTION

The invention is generally related to methods for atraumatic tooth extraction that utilize heat to degenerate periodontal ligament.

BACKGROUND OF THE INVENTION

Esthetics is a critical challenge in dental cases restored by implant-supported prostheses in the anterior maxilla.[1] This challenge relies on the integrity of the facial shelf of bone that is known to be a significant contributing factor to the esthetic of implant supported maxillary prosthesis.[2-6] Absence of the facial bone has a negative impact on the esthetic outcome of implant restorations[7] Immediate implant placement is mostly indicated when the labial cortical wall is intact.[4]

Traditional extraction protocols include traumatic luxation that often results in crack or fracture of the surrounding thin alveolar bone, particularly thin buccal walls; consequently bony defects are formed. These defects may preclude an optimum esthetic outcome with conventional fixed partial dentures or implant-supported prosthesis.[8] Atraumatic extraction practice is crucial to minimize damage to the buccal wall.[9] Several recommendations were proposed to preserve the facial bone during and after extraction. To avoid additional loss of buccal bone in sockets with thin facial bone, a flapless atraumatic tooth extraction with minimum force applied on buccal bone is recommended for immediate implant placement cases.[10,11] Other approaches of atraumatic extraction include the use of a periotome instrument, however, this instrument still relies on the wedging effect to separate the periodontal ligaments from the surrounding alveolar bone. A clinical study by Leblebicioglu, et al.,[12] evaluated the immediate post-extraction changes of ridge integrity following atraumatic extraction of 53 teeth in 30 adults. The study reported 9% post-extraction buccal plate fractures and 4% complete buccal plate loss.

Fracture of the buccal shelf of bone during extraction results in impairment of blood supply[13] leading to rapid resorption of labial plate and consequently soft tissue recession.[3] The thicker the labial plate is, the less resorption will occur.[4] Adequate thickness of buccal alveolar bone is essential for successful immediate implant placement particularly when no grafting procedure is intended.[14] A minimum thickness of intact 1 mm of labial plate is essential for immediate implant placement.[15,16]

Ghassemian et al.[14] evaluated the thickness of facial alveolar bone for the maxillary anterior teeth at a distance of 1 to 5 mm from the bone crest. The facial bone thickness was measured from sixty-six randomly selected tomographic scans of males and female patients, aged 17 to 69 years. The results of the study indicated that, at a level 3 mm from the CEJ, the average measured bone thickness was 1.41 mm and 1.45 mm for the maxillary right and left central incisors, respectively; 1.73 mm and 1.59 mm for the maxillary right and left lateral incisors, respectively; and, 1.47 mm and 1.60 mm for the maxillary right and left canines, respectively.

Nowzari et al.[17] measured the horizontal thickness of facial alveolar bone covering maxillary central incisors in 101 randomly selected cone beam computed tomography scan, at 1.0 mm increments apical to the bone crest. The results of the study reported an average thickness of 1.05 mm for right and left central incisors. The investigators reported that the prevailing concept for the need of at least 2 mm of facial bone implant placement in extraction sites was only available in 0, 1.5, 2.0, 3.0, and 2.5% at levels 1, 2, 3, 4, and 5 mm from the bone crest, respectively.

Several atraumatic extraction protocols were proposed to avoid luxation induced bony defects of the facial plate of bone during and after extraction. Flapless atraumatic tooth extraction was recommended for immediate implant placement cases to preserve the buccal shelf of bone.[10,11] Other approaches included the use of periotome instrument, which still relies on the wedging luxation to separate the periodontal ligaments from the surrounding alveolar bone.

Novel approaches to atraumatic tooth extractions that address the above disadvantages are needed.

SUMMARY

Disclosed herein are methods for atraumatic extraction utilizing a device to heat the periodontal ligament around the root of a tooth until degeneration of the periodontal ligament, after which extraction may be completed with minimum trauma/luxation of the surrounding alveolar bone.

An aspect of the disclosure provides a method for atraumatic tooth extraction comprising inserting an instrument into a pulp canal of a tooth, wherein the instrument comprises a body electrically connected to a heat providing source; and a tip arranged at one end of the body configured for insertion into a pulp canal; heating the tip to provide a temperature sufficient to degenerate periodontal ligament; withdrawing the instrument from the pulp canal; and extracting the tooth. In some embodiments, the method further comprises providing external irrigation using cooled water or gel as a cooling mechanism to control and limit increase of temperature of the periapical bone surrounding the tooth during and/or after the heating step.

In some embodiments, the tip has a length of 1-3 cm. In some embodiments, the tip has a diameter of 0.5-2.5 mm. In some embodiments, the heating step is performed by actuating a switch within the body for triggering heat generation. In some embodiments, after the heating step, the switch is actuated to provide for shut down and cooling of the tip. In some embodiments, the heat providing source is configured to provide a preset temperature and duration. In some embodiments, the tip is heated to a temperature sufficient to heat the periodontal ligament to a temperature of 45-47° C., wherein the temperature of the tip is a function of a cross-sectional root thickness of the tooth. In some embodiments, the preset temperature and duration is manually adjusted.

DETAILED DESCRIPTION

Embodiments of the disclosure provide a device and methods thereof which utilize thermal energy to facilitate atraumatic extraction by means of thermal degeneration/deligation of the periodontal ligaments by which the tooth/remaining root is attached to the alveolar bone. Thermal heating has been traditionally used in dentistry to inject molten root canal filling materials into the pulp space following root canal treatments. Unlike prior techniques, the methods of the present disclosure utilize heat to degenerate the periodontal ligament around the root of the tooth, after which extraction is completed with minimum trauma/luxation of the surrounding alveolar bone, thereby preserving the alveolar bone level to provide enough bone volume for implant stability and optimum esthetic.

Figure 1:
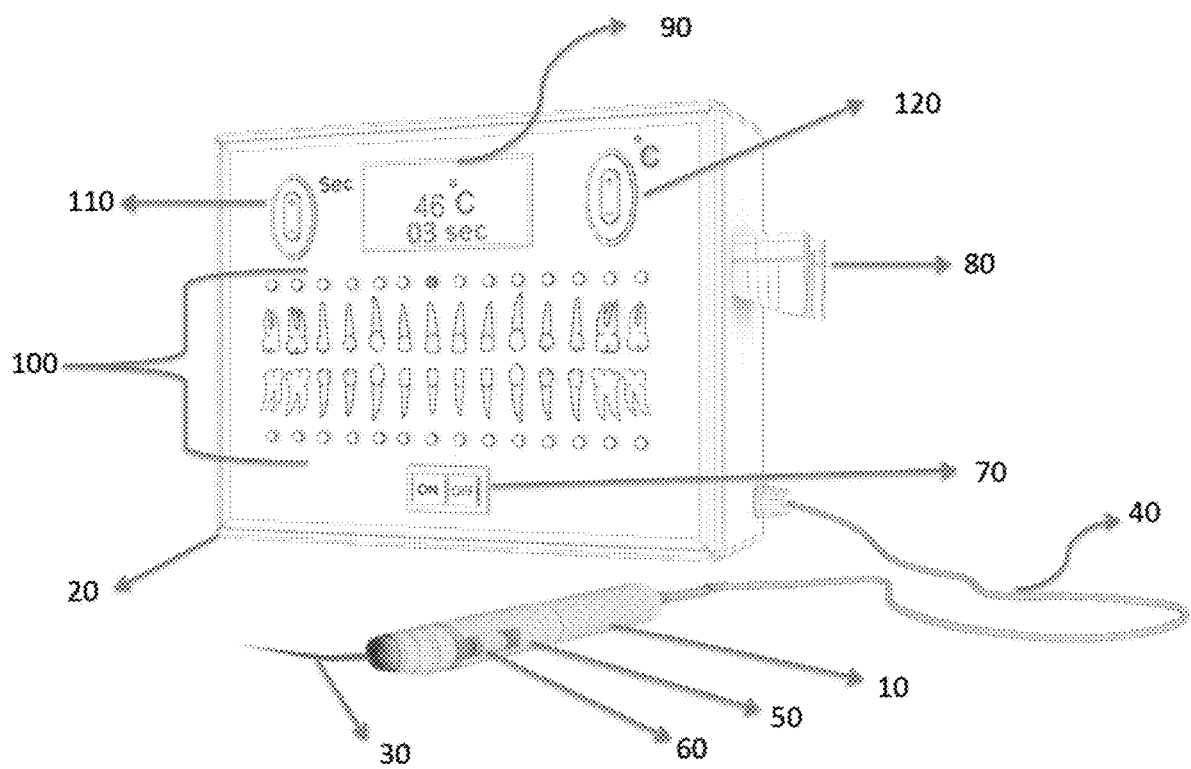
FIG. 1. An instrument for atraumatic tooth extraction according to some embodiments of the disclosure.
Figure 2:
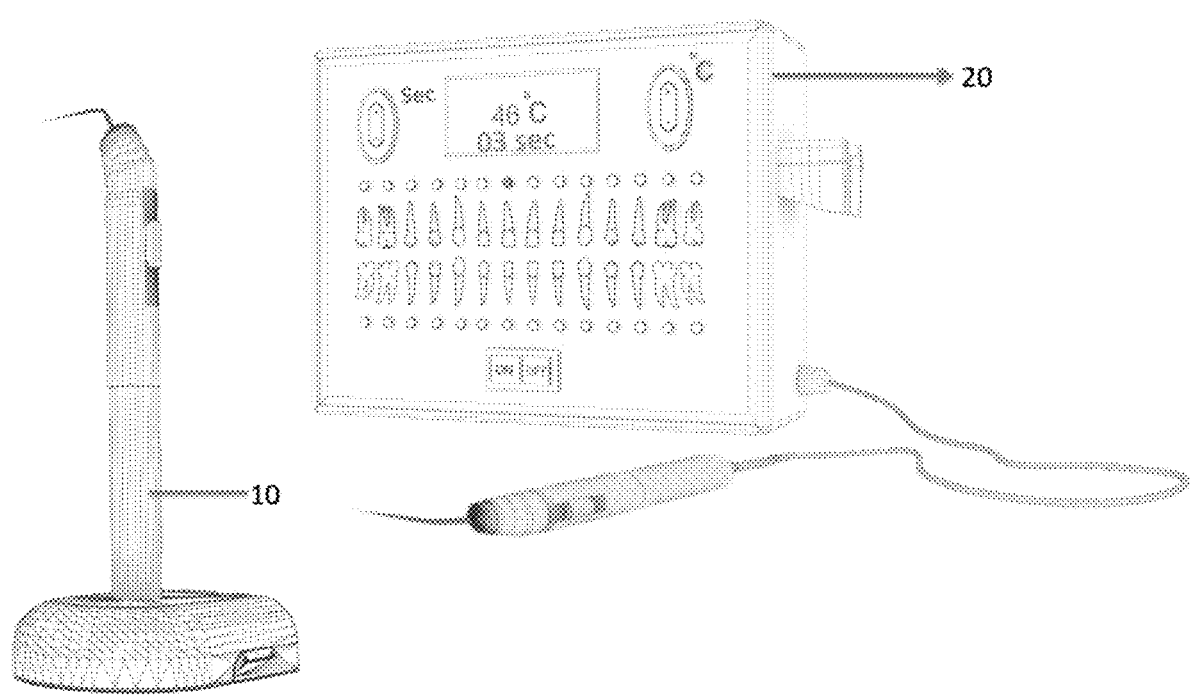
FIG. 2. An instrument for atraumatic tooth extraction according to additional embodiments of the disclosure.

With reference to FIG. 1, embodiments of the disclosure provide an instrument for atraumatic tooth extraction comprising a body 10 electrically connected to a heat providing source 20 (also referred to as an energy source or a power supply unit) and a tip 30 arranged at one end of the body configured for insertion into a pulp canal, wherein the tip is to be heated to distinct temperatures. In some embodiments, only one end of the body comprises a tip 30. The body 10 may be connected to the heat providing source 20 via a cable 40 or via a wireless connection (FIG. 2). The body 10 may further comprise a thermal insulator 50 for safe gripping.

The instrument may further comprise a switch 60 (e.g. a sliding switch) within the body 10 for triggering heat generation. In some embodiments, sliding the switch 60 towards the tip/nozzle 30 induces thermal conduction of the selected temperature gradient that is specific to the selected tooth of interest. In some embodiments, the switch 60 is further configured to provide for immediate shut down and instant cooling of the tip and thus acts as a safety mechanism. For example, sliding the switch 60 away from the tip/nozzle 30 may activate an instant emergency shutdown and cooling of the heated nozzle.

The heat providing source 20 may include a power switch 70, a body/handle rest 80, and a display 90 where the set time duration of heat application and target temperature at the periodontal ligament is displayed. The heat providing source 20 may also provide tooth/root selection controls 100 that allow for the selection of a particular tooth to optimize the temperature delivery according to a preprogrammed temperature based on calculations that are dependent on the reported dentin thickness of the tooth in concern.

The heat delivered is a function of the cross-sectional root thickness i.e. the distance from the center root canal where the tip resides to the outer surface of the root. The heat is delivered along the length of the root in a circumferential manner. The target temperature at the periodontal ligaments is to be set just below the documented temperature of bone necrosis that is 10° C. above body temperature. The goal is to degenerate the periodontal ligament while maintaining the integrity of alveolar bone. In some embodiments, the temperature delivered to the periodontal ligament is in the range of about 45-47° C., e.g. about 46° C., to avoid alveolar bone necrosis. In some embodiments, the temperature of the tip is 50-200° C., e.g. 100-150° C.

The temperature of the tip itself must be higher in order to deliver such target temperatures to compensate for the cross-sectional reduction of the root circumferential dentinal wall thickness in apical direction. The reduction in temperature is a function of the reduction of the cross sectional area of the root selected as implied by the laws of thermal diffusion. Thus, the method achieves a uniform heating along the periodontal ligament without undue over-heating in an area with reduced root thickness and consequently alveolar hone necrosis.

For example analysis of Lee et al. ("Three-Dimensional Analysis of Root Anatomy and Root Canal Curvature in Mandibular Incisors Using Micro-Computed Tomography with Novel Software", *Applied Sciences* 2020; 10: 4385) revealed an approximate 28% reduction of the circumferential cross-sectional dentin thickness from the apical portion of the cervical third of the canal to the apical portion of the middle third of the canal. In contrast, there was a 65.5% approximate reduction of the circumferential cross-sectional dentin thickness from the apical portion of the middle third of the canal to the apical portion of the apical third of the canal. Gradient reduction of the electrically induced heating of the device tip as a function of the cross sectional area of the root tissues thickness will reduce undue over heating induced damage to the alveolar bone that is in close proximity to the thinner wall of the root. Cross-sectional root tissue dimensions are not standardized between teeth (incisors, canines, . . . etc.) but average dimensions that are tooth/root specific may be obtained from Micro-Computed Tomography evaluation studies such as that implemented by Lee et al.

A time adjustment switch 110 may be provided to manually adjust the heating time for the selected root as shown on the display 90, if needed. A temperature adjustment switch 120 may be provided to adjust the heating temperature for the selected root as shown on the display 90. For example, pressing the (+) side of the switch will increase the delivered heat temperature to the selected root while pressing the (−) side of the switch will decrease the delivered heat temperature to the selected root. Thus, the preset temperature may be adjusted from the average preset values—which are established as a function of the average dentin thickness—to accommodate for any anatomical variation in the dentin thickness, such as those defects created by caries or resorption. In some embodiments, the heat providing source has a preset timer with safety limit to discontinue heat transmission in order to avoid undue thermal damage to the surrounding alveolar bone. The preset timer values may also be manually adjusted.

Figure 3:
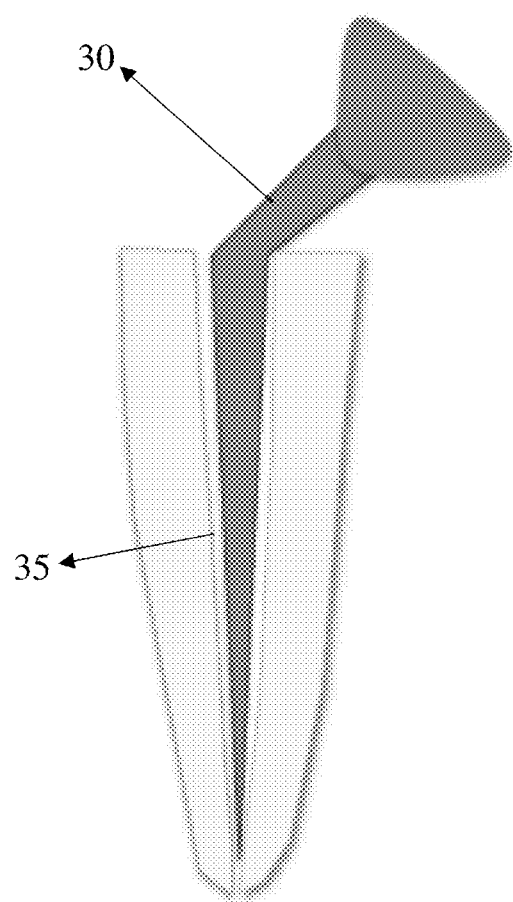
FIG. 3. A tip inserted into a pulp canal according to some embodiments of the disclosure.

With reference to FIG. 3, the tip/nozzle 30 may have a thin-walled elongated shape having a length of about 1.0-3.0 cm, e.g. 2.0 cm and an outer diameter of about 0.5-2.5 mm, e.g. 1.0-2.0 mm. The tip may be fabricated from a thermoconductive material. The tip 30 is configured for insertion into a root canal cavity 35. As shown in FIG. 3, the tip 30 may have an angular configuration, e.g. an L-shape, for ease of insertion.

Cooling of the priapical tissues to stop the heat from radiating beyond the periodontal ligament and consequently damaging the periapical tissues may be provided by external irrigation via an irrigating syringe filled with cooled water or gel. Such irrigating syringes are known in the art.

Methods for atraumatic tooth extraction may comprise inserting an instrument as described herein into a pulp canal of a tooth; utilizing heat to degenerate periodontal ligament; withdrawing the instrument from the pulp canal; and extracting the tooth.

Operation of the instrument may require drilling an access opening into the pulpal system and de-roofing the pulp chamber. When extracting a remaining root, the pulp canal is already open to access. The tip/nozzle is then inserted into pulp canal reaching the most apical constriction of the pulp canal foramen. The heating switch is then triggered to activate spontaneous conduction of thermal heat for the set duration. At the set time limit, an automatic instant shutdown of heat conduction occurs, followed by immediate cooling of the tip/nozzle to avoid undue tissue injury upon retrieval from the tooth and oral cavity. In some embodiments, the method further comprises external cooling by providing external irrigation using cooled water or gel as a cooling mechanism to control and limit increase of temperature of the periapical bone surrounding the tooth during and after the heating step. The external cooling may be provided by an irrigating syringe filled with cooled water or liquid gel. Cooling may commence prior to heat transmission and may continue for a few minutes post withdrawal of the tip from the pulp canal to ensure localized heat conduction to the periodontal ligaments with no injury to the surrounding bone.

An exemplary method of operation may comprise one or more of the following steps:

- Deliver a cooling solution on the mucosa surrounding the tooth to be extracted. Ensure proper circumferential cooling.
- Attach an appropriately sized nozzle/tip to the heat conducting device/body.
- Check the fit of the selected nozzle/tip by inserting it into the root canal cavity ensuring that the tip has reached the apical portion of the canal cavity.
- Turn the heat providing source on by turning the main operating switch to the ON position.
- Select the appropriate tooth from the tooth/root selection controls.
- The display monitor will indicate the set target temperature to degenerate the periodontal ligament. Adjust the temperature up or down if needed. Adjust the time up or down if needed.
- Wait until the selected tooth blinks on the tooth/root selection controls signaling that the apparatus is ready to deliver the heat.
- Slide the operating switch on the body towards the nozzle/tip in order to trigger heat conduction.
- Once the switch is activated, a beeping sound will resume ensuring active heat conduction. The frequency of the beeps will increase as proportional to the temperature rise. Once the set selected temperature of the selected tooth is reached, a steady beep will be heard.
- The steady beep will stop at the end of the preselected set time duration of heat conduction ensuring termination of heat conduction and commencing immediate cooling.
- The light of the selected tooth in the tooth/root selection controls will now turn off. Withdraw the nozzle/tip from the root.
- Turn the main operating switch to the OFF position.

If a less than average localized dentin thickness is observed in the radiograph, the user may utilize the temperature adjustment switch to adjust the heating temperature.

The instrument as described herein is particularly useful for extraction of teeth in the anterior esthetic segment where the thickness of buccal shelf of bone is small and where this bone thickness is a key factor for esthetic prosthetic restoration regardless of whether it is a fixed tooth supported or an implant supported prosthesis. Moreover, preservation of the buccal shelf of bone is a necessity for immediate implant placement. Restoration of the bony defect created by loss of the buccal plate of bone requires surgical procedures, which may necessitate harvesting bone graft from the palate, thereby generating another surgical site.

The instrument is also particularly useful for extraction of teeth with severely damaged coronal tooth structure that are difficult to grip and require surgical extraction and which in most cases exhibit an open pulp chamber created by the severe loss of coronal tooth structure. Severe caries of the coronal tooth structure may result in loss of the entire crown portion of the tooth rendering a non-restorable remaining tooth, which is difficult to grip, and requires extraction.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for atraumatic tooth extraction, comprising:
   measuring a cross-sectional root thickness of a tooth selected for extraction;
   inserting an instrument into a pulp canal of the tooth, wherein the instrument comprises
      a body electrically connected to a heat providing source; and
      a tip arranged at one end of the body configured for insertion into a pulp canal;
   heating the tip to provide a temperature sufficient to degenerate periodontal ligament, wherein the temperature of the tip is a function of the cross-sectional root thickness of the tooth such that an increased temperature is provided for an increased thickness;
   withdrawing the instrument from the pulp canal; and
   extracting the tooth.

2. The method of claim 1, further comprising providing external irrigation using cooled water or gel to limit an increase of temperature at a periapical bone surrounding the tooth during and/or after the heating step.

3. The method of claim 1, wherein the tip has a length of 1-3 cm.

4. The method of claim 1, wherein the tip has a diameter of 0.5-2.5 mm.

5. The method of claim 1, wherein the heating step is performed by actuating a switch within the body for triggering heat generation.

6. The method of claim 5, wherein after the heating step the switch is actuated to provide for shut down and cooling of the tip.

7. The method of claim 1, wherein the heat providing source is configured to provide a preset temperature and duration.

8. The method of claim 7, wherein the preset temperature and duration is manually adjusted.

9. The method of claim 1, wherein the tip is heated to a temperature sufficient to heat the periodontal ligament to a temperature of 45-47° C.

* * * * *